United States Patent [19]

Tazi et al.

[11] Patent Number: 5,147,941
[45] Date of Patent: Sep. 15, 1992

[54] DENTURE ADHESIVE

[75] Inventors: Mohammed Tazi, Wayne; Robert B. Login, Oakland; Krystyna Plochocka, Scotch Plains; Rama K. Haldar, Randolph; Balgopal Gangadharan, Caldwell; William E. Prosise, Ramsey, all of N.J.

[73] Assignee: ISP Investments Inc., Wilmington, Del.

[21] Appl. No.: 786,638

[22] Filed: Nov. 1, 1991

Related U.S. Application Data

[63] Continuation of Ser. No. 505,616, Apr. 6, 1990.

[51] Int. Cl.$^5$ ............................................. C08F 20/08
[52] U.S. Cl. .................................. 525/327.8; 523/120
[58] Field of Search ........................... 525/327.8, 120

[56] References Cited

U.S. PATENT DOCUMENTS 3,003,988 10/1961 Germann et al. ............... 525/327.8
4,929,690  5/1990 Goertz et al. .................. 525/327.8

Primary Examiner—Joseph L. Schofer
Assistant Examiner—Alex H. Walker
Attorney, Agent, or Firm—Walter Katz; Marilyn J. Maue; Joshua J. Ward

[57] ABSTRACT

According to this invention, there is provided a denture adhesive which is a mixed partial salt of a copolymer of maleic anhydride and acrylic acid (or methacrylic acid), optionally including a $C_1$–$C_4$ alkyl vinyl ether, having a weight average molecular weight of about 30,000 to 400,000, preferably about 50,000 to 350,000. The copolymer comprises about 10 to 70 mole percent, preferably 20 to 60 mole percent, of maleic anhydride, about 30 to 90 mole percent, preferably 40 to 80 percent, of acrylic acid (or methacrylic acid), and 0 to 25 mole percent of a $C_1$–$C_4$ alkyl vinyl ether.

7 Claims, 1 Drawing Sheet

DENTURE ADHESIVE

This is a continuation of application Ser. No. 505,616, filed Apr. 6, 1990.

BACKGROUND OF THE INVENTION

1. Field of the Invention

This invention relates to denture adhesives of mixed partial salts of copolymers of maleic anhydride and acrylic acid, and particularly to denture adhesive compositions thereof.

2. Description of the Prior Art

Various adhesive compositions have been employed for fixing dentures. U.S. Pat. Nos. disclosing such compositions include 3,003,988; 3,736,274; 3,740,361; 3,833,518; 3,868,339; 3,868,432; 4,183,914; 4,217,342; 4,217,343; 4,521,551 and 4,758,630. Such denture adhesive compositions, however, are found to be effective for only a limited time of up to 8 hours and some for as little as 2 or 3 hours.

Accordingly, it is an object of this invention to provide a denture adhesive composition having both initial stick force strength and long term performance characterized by prolonged adhesion properties.

Another object herein is to provide a mixed partial salt of maleic anhydride-acrylic acid copolymer, optionally including a $C_1$-$C_4$ alkyl vinyl ether, having effective strength properties for use as a denture adhesive.

These and other objects and features of the invention will be made apparent from the following disclosure and description.

DESCRIPTION OF THE DRAWINGS

The FIGURE is a graph of adhesive force in lbs. vs. number of cycles during Instron testing of adhesive compositions of the invention.

SUMMARY OF THE INVENTION

Figure 1:
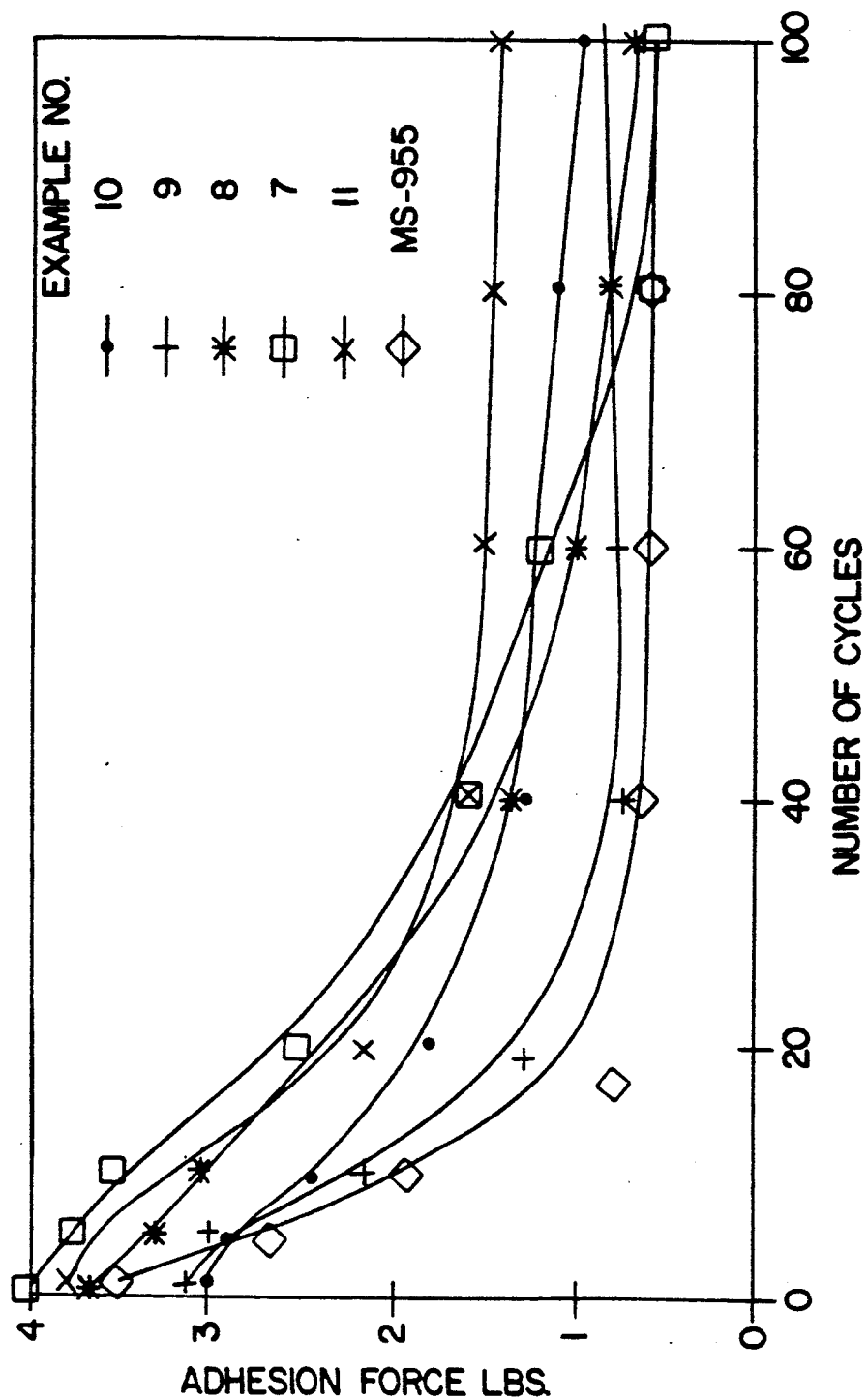

According to this invention, there is provided a denture adhesive which is a mixed partial salt of a copolymer of maleic anhydride and acrylic acid (or methacrylic acid), optionally including a $C_1$-$C_4$ alkyl vinyl ether, having a weight average molecular weight of about 30,000 to 400,000, preferably about 50,000 to 350,000.

The copolymer suitably comprises about 10 to 70 mole percent, preferably 20 to 60 mole percent, of maleic anhydride, about 30 to 90 mole percent, preferably 40 to 80 percent, of acrylic acid (or methacrylic acid), and 0 to 25 mole percent of a $C_1$-$C_4$ alkyl vinyl ether.

The partial mixed salts include calcium/sodium salts wherein the equivalent ratio of calcium to sodium cations may range from 2:1 to 10:1, preferably between 3:1 to 7:1, and the degree of neutralization of initial carboxyl groups is from 0.5 to 0.95, preferably from 0.7 to 0.9.

DETAILED DESCRIPTION OF THE INVENTION

The copolymer of the invention is made by polymerizing the monomers in the presence of a free radical initiator, at about 50° to 150° C., and usually about 60° to 80° C. Preferably, polymerization is carried out in a solvent, such as cyclohexane, although most preferably, a cosolvent system is used which comprises about 5 to 80 percent by weight, preferably 10 to 75 percent, of ethyl acetate, and about 20 to 95 percent by weight, preferably 25 to 90 percent by weight, of an aliphatic or cycloaliphatic hydrocarbon having a boiling point of at least 10° C. above the reaction temperature, which is preferably cyclohexane. In this cosolvent system, a pumpable slurry of the copolymer in the cosolvent is produced, from which the copolymer can be recovered readily as a uniform, fine white powder having substantially no residual maleic anhydride.

The adhesive copolymer of this invention is converted to its mixed partial salt, which preferably is employed as a dry powder having a particle size of less than 250 $\mu$, and, more desirably, a particle size of from about 5 to about 200 $\mu$.

Denture adhesive compositions are provided herein by incorporating dry powders of the above adhesive copolymer as mixed salts into a liquid base carrier by mixing until a homogeneous cream paste suspension or collodial dispersion is obtained, usually within a period of from about 20 minutes to about 5 hours. The resulting composition contains an effective adhesive amount of the adhesive copolymer mixed salt, generally between about 5 and about 50 wt. %, and preferably between about 10 and about 35 wt. %, of the final composition.

Suitable mixed partial salts herein include the calcium/sodium mixed partial salts which are prepared by reacting the copolymer with suitable bases. Preferably the equivalent ratio of calcium cations to sodium cations in the mixed partial salts may range from 2:1 to 10:1 and most preferably is between 3:1 and 7:1 (on a mole ratio basis, the range of calcium to sodium cations is from 1:1 to 5:1, most preferably from 1.5:1 to 3.5:1). The sum total of cations in the mixed partial salt should be sufficient to give a degree of neutralization of from 0.5 to 0.95 and preferably 0.7 to 0.9 of the total initial carboxyl groups in the copolymer. In the determination of the total initial carboxyl groups in the copolymer, the anhydride radical is considered as containing 2 initial carboxyl groups.

The base carrier portion of the composition generally includes a water soluble or partially water soluble hydrophilic carrier which is capable of swelling upon exposure to moisture to form a mucilaginous mass. Such carrier materials include natural and synthetic gums, viscous liquids, gels and powders. Among those suitably employed as base carriers in the composition are karaya gum, gelatine, gum tragacanth, gum acacia, gum shiraz, algin, sodium alginate, tragacanth, methyl cellulose, a mixture of petrolatum and mineral oil, glycerine, polyvinylpyrrolidone, K-30 and K-90, carboxymethyl cellulose, ethylene oxide polymers, of which the preferred is a mixture of petrolatum and mineral oil in a ratio of 40:60–60:40.

The adhesive copolymer of the invention can be employed as the sole adhesive component in the denture adhesive composition or it can be used as a coadhesive with another adhesive material. Such adhesive additive, if present, will generally comprise about 5–20% by weight of the composition. Suitable adhesive additives include natural or synthetic polymers such as cellulose, karaya gum, gum tragacanth, gum acacia, carboxymethyl cellulose or salt thereof, polymethacrylate, polyvinylpyrrolidone, polyvinyl acetate, or any mixture of the above.

The compositions of the invention are particularly useful for affixing dentures and can also be used in surgical procedures which require temporary displacement of tissue. As a denture adhesive, the thermal stability of the present composition, over a temperature range which is at least sufficient to embrace all conditions encountered by living tissue, e.g. 5°–50° C., is particularly desirable. Because of their increased adhesive strength and thermal stability, the composition retains its adhesive properties over a long period of time, i.e. up to 24 hours.

The following illustrates a few representative formulations into which the adhesive copolymer can be added in effective amounts up to about 50%.

|  | wt. % |
|---|---|
| Cream Denture Adhesive Composition | |
| Mineral Oil | 30 |
| Petrolatum | 25 |
| Sodium carboxymethyl cellulose (adhesive additive) | 20 |
| Colorant | 1 |
| Flavoring Agent | 0.5 |
| Material of Invention | 23.5 |
| Paste Ostomy Adhesive Composition | |
| Mineral oil (heavy) | 35 |
| Glycerine | 5 |
| Polyvinylpyrrolidone | 20 |
| Carboxymethyl cellulose | 5 |
| Tosylate of quat. amino-N-propylpyrrolidone | 0.5 |
| Material of Invention | 34.5 |
| Denture Adhesive Powder Composition | |
| Gum tragacanth | 40 |
| Gum acacia | 20 |
| Spearmint oil | 0.05 |
| Material of Invention | 39.05 |

Reference is now made to the following examples which provide preferred embodiments of the invention.

EXAMPLE 1

Preparation of Copolymer

A 1-liter resin kettle was equipped with a stirrer, reflux condenser, a $N_2$ inlet tube and an inlet closed with a rubber septum for introduction of a polymerization initiator. The kettle was charged with 49.0 g. (0.50 mole) of maleic anhydride (MA), 275 g. (75 wt. %) of ethyl acetate (EA) and 92 g. (25 wt. %) of cyclohexane (CH). Agitation of the mixture was begun and the system was purged by bubbling in $N_2$ for 30 minutes, during which time the maleic anhydride dissolved completely. The reaction mixture was then warmed to 65° C. and 0.3 ml of Lupersol 11 (Pennwalt) was injected through the septum to initiate polymerization. Simultaneously, dropwise addition of 73.0 g. (1.0 mole) of acrylic acid (AA) was begun and continued over a period of 3 hours. Lupersol 11 was added at a rate of 0.3 ml of initiator for each 30 minutes of AA addition during this period. After completion of all additions, the resulting mixture was maintained at 65° C. for 2 hours.

After 15 minutes the reaction mixture became whitish, and, thereafter, a uniformly thick, creamy slurry was formed which was pumped out of the kettle into a filtration unit. There the slurry was filtered and the polymer product was dried for about 12 hours at 65° C. in a forced air oven. The polymer product was a uniform, fine white powder, having a weight average molecular weight (as determined by GPC) of about 47,000. A sample of 1 g. of the polymer dissolved in 5 ml acetone was treated with triphenyl phosphine and it indicated that conversion of maleic anhydride into polymer was complete.

EXAMPLES 2–11

The procedure of Example 1 was followed to provide copolymers of varying compositions and molecular weights. The results of Examples 1–11 are shown in Table 1 below. In Examples 9 and 10 therein, a third monomer, either butyl vinyl ether or methyl vinyl ether, was introduced after addition of acrylic acid was completed.

Preparation of Denture Adhesive Compositions of Invention

The copolymer of Example 11 was converted to its mixed, partial salts as follows. 25 g. of the copolymer was charged into a 250 ml round bottom, 3-necked flask together with 90 g. of isopropyl alcohol. The contents were agitated to make a slurry and 9.59 g. of calcium hydroxide was added slowly with agitation during 15 minutes. Then 2.08 g. of sodium hydroxide dissolved in 38 g. of water was added with agitation. The mixture was heated at 45° C. with agitation for 1½ hours. The pH of the liquid phase was 4.89. The mixture was filtered and the precipitate was dried in a vacuum oven overnight at 65° C. Similar copolymer conversions to the mixed partial salts were effected for the copolymers of Examples 1–10.

EXAMPLE 12

Preparation of Adhesive Compositions for Instron Testing

The dry, mixed salt of the MA/AA copolymer of Example 11 was milled to pass through a number 60 mesh sieve (250 μ) and the resulting powder was then dispersed at a temperature of 55°–65° C., followed by cooling to 20°–25° C., into a petrolatum base using mechanical stirring. The ratio of copolymer to base by weight was 1:2. The resulting cream dispersion was collected as the desired adhesive composition.

EXAMPLE 3

Adhesive compositions of the dry, mixed salt of the copolymers of Examples 1–10, and GANTREZ MS-955, which is a commercial mixed salt copolymer of maleic anhydride and methyl vinyl ether, also were prepared for testing in the same manner as described above for Example 11.

EXAMPLE 14

2 g. samples of each of the above prepared compositions were evaluated for adhesion characteristics by Instron testing according to the following procedure:

In the first step, the upper and lower plates of the Instron apparatus were brought together to obtain a zero position. The upper plate was then raised 0.06 inch and the upper cycle limit on the Instron indicator is set at this point. The upper plate was then lowered and the lower cycle limit was set. In its lowest position, the upper plate was distanced 0.03 inch above the lower plate.

With these Instron settings determined, the upper plate was then raised and 2 g. of the test sample was uniformly spread over the surface of the lower plate in a 1/16 to ⅛ inch thickness; thereafter simulated salivary fluid was applied over the sample so that it was barely covered.

The Instron crosshead was cycled between the previously set limits at a crosshead speed of 0.2 in./min. The Instron chart was set in the continuous mode at a speed of 2 in./min. to record the compression and adhesion force for each cycle, 5 to 100 cycles.

At the end of 100 cycles, the motion of the upper plate was halted and raised high enough to clean the surface before the next adhesive test.

Each recording was analyzed and the adhesional forces (lbs.) for the 1st, 5th, 10th, 20th, 40th . . . 100th cycles were recorded and then plotted graphically.

The results of this study are shown in the FIGURE. This data show significantly better initial stick strength and long term adhesion for adhesive formulations containing the copolymer compositions of the invention as compared to a related copolymer composition (MS-955) useful as a denture adhesive.

While the invention has been described with particular reference to certain embodiments thereof, it will be understood that changes and modifications may be made which are within the skill of the art. Accordingly, it is intended to be bound only by the following claims, in which:

What is claimed is:

1. A denture adhesive composition consisting essentially of about 5 to 50 weight percent of a mixed, partial salt of a copolymer of (a) about 20 to 60 mole percent of maleic anhydride, (b) about 40 to 80 mole percent of acrylic acid or methacrylic acid, and (c) 0 to 25 mole percent of a $C_1$–$C_4$ alkyl vinyl ether, said copolymer having a weight average molecular weight of about 100,000 to 400,000, and a base carrier which is a water soluble or partially water soluble hydrophilic carrier capable of swelling upon exposure to water to form a mucilaginous mass, and wherein the sum total of cations in the mixed partial salt is sufficient to give a degree of neutralization of from 0.5 to 0.95 of the total initial carboxyl groups in the copolymer.

2. A composition according to claim 1 which includes about 5 to 20% by weight of an adhesive additive which is a natural or synthetic polymer.

3. A composition according to claim 2 wherein said polymer adhesive additive is karaya gum or carboxymethyl cellulose.

4. A denture adhesive composition according to claim 1 wherein the mixed, partial salt is a calcium/sodium salt.

5. A denture adhesive composition according to claim 4 wherein the calcium to sodium cation equivalent ratio is 2:1 to 10:1.

6. A denture adhesive composition according to claim 5 wherein the ratio is 3:1 to 7:1.

7. A denture adhesive composition according to claim 1 wherein said sum total is 0.7 to 0.9.

* * * * *

UNITED STATES PATENT OFFICE
CERTIFICATE OF CORRECTION

Patent No. 5,147,941    Dated Sep. 15, 1992

Inventor(s) Mohammed Tazi et al.

It is certified that error appears in the above-identified patent and that said Letters Patent is hereby corrected as shown below:

In column 4, before EXAMPLE 12, TABLE 1 was not included in the printing of the patent. Please insert TABLE 1, as per attached.

In column 4, line 40 "EXAMPLE 3" should read --- EXAMPLE 13 ---.

Signed and Sealed this

Eleventh Day of January, 1994

BRUCE LEHMAN

Commissioner of Patents and Trademarks

TABLE 1

| Ex. No. | Monomers AA | MA | Other | Solvent EA | CH | Initiator** | Temp. | Weight Average Molecular Wt, Mw |
|---|---|---|---|---|---|---|---|---|
| | (mole %) | | | (wt %) | | (% by wt) | (°C.) | (x $10^3$) |
| 1 | 66 | 33 | - | 75 | 25 | L-11; 0.3 | 65 | 47 |
| 2 | 66 | 33 | - | 25 | 75 | L-11; 0.4 | 65 | 145 |
| 3 | 50 | 50 | - | 25 | 75 | L-11; 0.4 | 65 | 79 |
| 4 | 57 | 43 | - | 50 | 50 | L-11; 3.2 | 65 | 19 |
| 5 | 57 | 43 | - | 25 | 75 | L-11; 0.8 | 65 | 59 |
| 6 | 57 | 43 | - | 25 | 75 | Dec-F; 0.4 | 75 | 202 |
| 7 | 57 | 43 | - | 25 | 75 | L-PMS; 0.4 | 75 | 110 |
| 8 | 80 | 20 | - | 10 | 90 | L-11; 0.25 | 65 | 310 |
| 9 | 45 | 33 | 22 BVE* | 50 | 50 | L-11; 3.2 | 65 | 16 |
| 10 | 67 | 17 | 16 MVE* | 10 | 90 | L-11; 0.4 | 60 | 337 |
| 11 | 80 | 20 | - | - | 100 | L-11; 0.0 | 65 | 345 |

\* BVE - butyl vinyl ether; * MVE - methyl vinyl ether
\*\* L-11 - t-butyl perpivalate, L-PMS - t-butyl peroctoate, Dec-F - decanoyl peroxide